US011883505B2

(12) United States Patent
Steinmetz et al.

(10) Patent No.: US 11,883,505 B2
(45) Date of Patent: *Jan. 30, 2024

(54) ANTICANCER DRUG-CONTAINING PLANT VIRUS PARTICLES

(71) Applicants: CASE WESTERN RESERVE UNIVERSITY, Cleveland, OH (US); MASSACHUSETTS INSTITUTE OF TECHNOLOGY, Cambridge, MA (US)

(72) Inventors: Nicole F. Steinmetz, San Diego, CA (US); Stephen J. Lippard, Cambridge, MA (US); Anna Czapar, Cleveland, OH (US); Yaorong Zheng, Cambridge, MA (US)

(73) Assignees: CASE WESTERN RESERVE UNIVERSITY, Cleveland, OH (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/854,444

(22) Filed: Apr. 21, 2020

(65) Prior Publication Data
US 2020/0246482 A1    Aug. 6, 2020

Related U.S. Application Data

(63) Continuation of application No. 15/741,017, filed as application No. PCT/US2016/039961 on Jun. 29, 2016, now Pat. No. 10,624,975.

(60) Provisional application No. 62/201,227, filed on Aug. 5, 2015, provisional application No. 62/185,881, filed on Jun. 29, 2015.

(51) Int. Cl.
| | |
|---|---|
| *A61P 35/00* | (2006.01) |
| *A61K 9/19* | (2006.01) |
| *A61K 31/555* | (2006.01) |
| *A61K 39/12* | (2006.01) |
| *A61K 47/69* | (2017.01) |
| *A61K 9/00* | (2006.01) |
| *A61K 9/51* | (2006.01) |
| *A61K 39/00* | (2006.01) |

(52) U.S. Cl.
CPC ........ *A61K 47/6901* (2017.08); *A61K 9/0019* (2013.01); *A61K 9/5184* (2013.01); *A61K 31/555* (2013.01); *A61K 39/12* (2013.01); *A61P 35/00* (2018.01); *A61K 2039/585* (2013.01); *C12N 2750/12022* (2013.01); *C12N 2750/12023* (2013.01); *C12N 2770/00034* (2013.01); *C12N 2770/00042* (2013.01); *C12N 2770/32022* (2013.01); *C12N 2770/32023* (2013.01)

(58) Field of Classification Search
CPC .............. A61K 47/6901; A61K 9/0019; A61K 9/5184; A61K 31/555; A61K 39/12; A61P 35/00
See application file for complete search history.

(56) References Cited

U.S. PATENT DOCUMENTS

| | | | |
|---|---|---|---|
| 5,004,606 A | 4/1991 | Frincke | |
| 9,925,281 B2 | 3/2018 | Steinmetz et al. | |
| 10,086,095 B2 | 10/2018 | Steinmetz et al. | |
| 10,207,014 B2 | 2/2019 | Steinmetz et al. | |
| 10,478,510 B2 | 11/2019 | Steinmetz | |
| 11,020,497 B2 | 6/2021 | Steinmetz et al. | |
| 11,167,047 B2 | 11/2021 | Steinmetz et al. | |
| 11,253,610 B2 | 2/2022 | Steinmetz | |
| 2005/0019270 A1 | 1/2005 | Finlay et al. | |
| 2007/0248617 A1 | 10/2007 | Bachmann et al. | |
| 2007/0258889 A1 | 11/2007 | Douglas et al. | |
| 2007/0284545 A1 | 12/2007 | Isacsson et al. | |
| 2010/0183504 A1 | 7/2010 | Chen | |
| 2015/0033418 A1 | 1/2015 | Lommel et al. | |
| 2015/0265696 A1 | 9/2015 | Gourapura et al. | |
| 2020/0179468 A1 | 6/2020 | Steinmetz | |
| 2022/0211881 A1 | 7/2022 | Steinmetz | |

FOREIGN PATENT DOCUMENTS

| | | |
|---|---|---|
| JP | 2009524699 A | 7/2009 |
| WO | 01/18199 A1 | 3/2001 |
| WO | 2001/0026682 A2 | 4/2001 |
| WO | 2003092623 A2 | 11/2003 |
| WO | 2012078069 A1 | 6/2012 |
| WO | 2013181557 A1 | 12/2013 |

(Continued)

OTHER PUBLICATIONS

Bruckman et al., "Chemical Modification of the Inner and Outer Surfaces of Tobacco Mosaic Virus (TMV)," Methods Mol Biol 2014; 1108: 173-185 (Protocol first published online Oct. 30, 2013).*
Kelland, "Broadening the clinical use of platinum drug-based chemotherapy with new analogues," Jun. 26, 2007. (Year: 2007).*
Johnstone TC, Park GY, Lippard SJ. Understanding and improving platinum anticancer drugs—phenanthriplatin. Anticancer Res. Jan. 2014;34(1):471-6. (Year: 2014).*
Adams, MJ et al. Virgaviridae: a new family of rod-shaped plant viruses. Arch Virol. Oct. 28, 2009. vol. 154; abstract; DOI; 10.1007/s00705-009-05069-6.

(Continued)

*Primary Examiner* — Jared Barsky
(74) *Attorney, Agent, or Firm* — TAROLLI, SUNDHEIM, COVELL & TUMMINO, LLP

(57) ABSTRACT

Anticancer virus particles are described. Anticancer virus particles are filamentous or rod-shaped plant virus particle containing an anticancer agent within the interior of the virus particle. The anticancer agent can be attached either covalently or non-covalently within the interior of the virus particle. A therapeutically effective amount of an anticancer virus particle can be administered to a subject identified as having cancer to provide a method of cancer treatment.

12 Claims, 12 Drawing Sheets

(56) References Cited

FOREIGN PATENT DOCUMENTS

| WO | WO-2013181557 A1 * | 12/2013 | ......... A61K 49/0002 |
|---|---|---|---|
| WO | 2014059021 A1 | 4/2014 | |
| WO | 2014113203 A1 | 7/2014 | |
| WO | 2014130454 A1 | 8/2014 | |
| WO | 2015/039255 A1 | 3/2015 | |
| WO | 2015/188110 A1 | 12/2015 | |
| WO | 2016019393 A1 | 2/2016 | |
| WO | 2016/073972 A1 | 5/2016 | |
| WO | 2016073972 A1 | 5/2016 | |
| WO | 2016/149264 A1 | 9/2016 | |
| WO | 2017/004123 A1 | 1/2017 | |

OTHER PUBLICATIONS

Park, GY, et al. Phenanthriplatin, a monofunctional DNA-binding platinum anticancer drug candidate with unusual potency and cellular activity profile. PNAS. Jul. 24, 2012. vol. 109, No. 30; abstract; p. 19987, col. 1, paragraphs 102; DOI: 10.1073/pnas. 1207670109.

Applicant: Case Western Reserve University; "Cancer Immunotherapy Using Virus Particles"; European Patent Application No. 18764856.3 for Supplementary European Search Report dated Dec. 22, 2020; 8 pgs.

Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.

Nicole F.Steinmetz; "Viral Nanoparticle Multimers"; U.S. Appl. No. 14/761,444, filed Jul. 16, 2015; Final Office Action dated Mar. 11, 2021; 11 pgs.

Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.

Applicant: Case Western Reserve University; "Cancer Immunotherapy Using Virus Particles"; Office Action, dated Aug. 4, 2020; 3 pgs.

Applicant: Case Western Reserve University; "Plant Virus Particles for Delivery of Antimitotic Agents"; Extended European Search Report; dated Aug. 17, 2020; 11 pgs.

Office action for Japanese Patent Application No. 2017-524349, dated Jan. 31, 2020.

Yildiz et al., "Applications of viral nanoparticles in medicine", Current Opinion in Biotechnology, vol. 22, Issue 6, pp. 901-908.

Aljabali, et al., "CPMV-DOX Delivers", Molecular Pharmaceutics, 2013, 10, pp. 3-10.

Wen, et al., "Interior Engineering of a Viral Nanoparticle and its Tumor Homing Properties" Macromolecules, vol. 13, No. 12, Dec. 2012.

Agrawal, et al., "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012.

Brennan, et al., "Cowpea Mosaic Virus as a Vaccine Carrier of Heterologous Antigens", Molecular Biotechnology, vol. 17, No. 1, Jan. 2001.

Gonzalez, et al., "Interaction of Cowpea Mosaic Virus (CPMV) Nanoparticles with Antigen Presenting Cells in Vitro and In Vivo", PLOS ONE, vol. 4, No. 11, Nov. 2009.

Lizotte, et al., "Plant-derived viral-like nanoparticle immunotherapy suppress development of metastatic lung cancer", Journal of Immunology, vol. 194, Issue 1 Supplement, May 2015.

Patrick H. Lizotte, "Novel approaches to targeting innate immunity for cancer immunotherapy", Proquest Dissertations Publishing, May 2015.

Supplementary European Search Report for Patent Application No. 15857504.3-1111/3215520, dated May 28, 2018.

International Search Report for Application No. PCT/US15/59675. Plchova et al. Expression of Human papillomavirus 16 E7ggg oncoprotein on N- and C-terminus of Potato virus X coat protein in bacterial and plant cells. Protein Expression and Purification 77 (2011) 146-152.

"CWRU researcher to turn plant virus shells against human cancers", The Daily, CWRU Researcher to Turn Plant Virus Shells Against Human Cancers. Case Western Reserve University, Apr. 18, 2016.

Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.

Alaa A. AL. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.

Applicant: Case Western Reserve University; "Cancer Immunotherapy Using Virus Particles"; Canadian Office Action, dated Aug. 4, 2020; 3 pgs.

Applicant: Case Western Reserve University; "Cancer Immunotherapy Using Virus Particles"; European Patent Application No. 21201960. 8; Extended European Search Report dated Jan. 19, 2022; 11 pgs.

Applicant: Case Western Reserve University; "Plant Virus Particles for Delivery of Antimitotic Agents"; Extended European Search Report; dated Aug. 25, 2020; 11 pgs.

Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.

Canan Uluog, et al.: "Intermediate dose of methotrexate toxicity in non-Hodgkin lymphoma", General Pharmacology, vol. 32, 1999, pp. 215-218, XP55711259.

Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 18, 2015; 26(2): 262-269.

European Search Report for Patent Application No. 15857504.3-1111/3215520, dated May 7, 2018.

Francisco, Joseph A., et al.; "cAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.

Gonzalez Maria Jet al: "Interaction of Cowpea Mosaic Virus (CPMV) Nanoparticles with Antigen Presenting Cells In Vitro and In Vivo", PLOS ONE, vol. 4, No. 11, Nov. 2009 (Nov. 2009), XP002780311, ISSN: 1932-6203.

International Search Report for Application No. PCT/US15/59675 (dated 2016).

Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.

Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.

Lee et al. "Biodegradable Viral Nanoparticle/Polymer Implants Prepared via Melt-Processing", ACS Nano ePub Sep. 13, 2017 vol. 11 No. 9 pp. 8777-8780.

Lee et al., "PEGylation to Improve Protein Stability During Melt Processing", Macromol Biosci 1-43, 57-75, Oct. 2015 vol. 15 No. 10 pp. 1332-1337.

Lizotte, et al., "Plant-derived viral-like nanoparticle immunotherapy suppress development of metastatic lung cancer", Journal of Immunology, vol. 194, Issue 1 Supplement, May 2015; 4 pgs.

Matsuura et al. Self-assembly of Ni-NT A-modified [3-annulus peptides into artificial viral capsids and encapsulation of His-tagged proteins. Org. Biomol. Chem., 2016, 14, 7869. DOI: 10.1039/c6ob01227b (Year: 2016).

Miermont et al., "Cowpea Mosaic Virus Capsid: A promising Carrier for the Development of Carbohydrate Based Antitumor Vaccines", Chem. Eur. J., 2008, vol. 14, pp. 4939-4947.

Nicole F. Steinmetz; U.S. Appl. No. 16/347,503, filed May 3, 2019; NonFinal Rejection dated Jun. 15, 2022; 36 pgs.

(56) References Cited

OTHER PUBLICATIONS

Nicole F. Steinmetz; U.S. Appl. No. 16/614,676, filed Nov. 18, 2019; NonFinal Rejection dated Jun. 3, 2022; 28 pgs.
Office action for Chinese Patent Application No. 201580063662.6, dated Mar. 4, 2020.
Office action for European Patent Application No. 15 857 504.3-1111, dated Mar. 18, 2020.
Office action for Japanese Patent Application No. 2017-524349, drafted Jan. 31, 2020; dated Feb. 10, 2020; 6 pgs.
Patrick h. lizotte: "Novel approaches to targeting innate immunity for cancer immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].
Plchova et al. Expression of Human papillomavirus 16 E7ggg oncoprotein on N- and C-terminus of Potato virus X coat protein in bacterial and plant cells. Protein Expression and Purification 77 (2011); p. 146-152.
Saunders K et al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].
Sheen et al., "Stimulating Antitumor Immunity with Nanoparticles", Wiley Interdiscip Rev Nanomed Nanobiotechnol, Oct. 2014, vol. 6, pp. 496-505.
Smyth et al. Treatment of rapidly growing K-BALB and CT26 mouse tumours using Semliki Forest virus and its derived vector. Gene Therapy (2005) 12, 147-159.
Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.
Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.
Wen et al. Design of virus-based nanomaterials for medicine, biotechnology, and energy. Chem. Soc. Rev., 2016, 45, 4074. DOI: 10.1039/c5cs00287g (Year: 2016).
Yildiz, et al., "Applications of viral nanoparticles in medicine", Current Opinion in Biotechnology, vol. 22, Issue 6, (2011); pp. 901-908.
Chinese Patent Appl. No. 201580063662.6; Chinese Office Action; dated May 5, 2022; 3 pgs.
Czapar, Anna et al. Tobacco Mosaic Virus Delivery of Phenanthriplatin for Cancer therapy. American Chemical Society. Nano 2016 (10) pp. 4119-4126 (Year: 2016).
Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).
Le, Duc et al. Chemical addressability of potoato virus X for its applications in bio/nanotechnology. El Sevier. Journal of Structural Biology 200 (2017). pp. 360-368. (Year: 2017).
Le, Duc et al. Potato virus X, a filamentous plant viral nanoparticle for doxorubicin delivery in cancer therapy. Royal Society of Chemistry. Nanoscale, 2017 (9). pp. 2348-2357. (Year 2017).
Nicole F. Steinmetz, U.S. Appl. No. 16/998,210, filed Aug. 7, 2020; Non-Final OA dated Dec. 7, 2022.
Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).
Bruckman et al. (Nano Letters. Mar. 2014; 14: 1551-1558).
Imamura et al. ("FOXA 1 promotes tumor progression in prostate cancer via the insulin-like growth factor binding protein 3 pathway." (2012)).
Lam, et al. (WIREs Nanomed Nanobiotechnol Jan./Feb. 2018 vol. 10: 1-18).
Mitoxantrone. Drug Bank Online. Website. https://go.drugbank.com/drugs/DB01204. (Accessed Dec. 15, 2022) (Year: 2022).
Mosquera et al. (Acc. Chem. Res. 2018, 51, 9, 2305-2313 Publication Date: Aug. 29, 2018.
Nicole F.Steinmetz; U.S. Appl. No. 16/597,509, filed Oct. 9, 2019; Non-Final Office Action, dated Dec. 27, 2022; 12 pgs.
Nicole F.Steinmetz; U.S. Appl. No. 16/759,652, filed Apr. 27, 2020; Final Office Action, dated Dec. 12, 2022; 15 pgs.
Nicole F.Steinmetz; U.S. Appl. No. 17/129,463, filed Dec. 21, 2020; Non-Final Office Action, dated Dec. 8, 2022; 32 pgs.
Nicole F.Steinmetz; U.S. Appl. No. 17/522,182, filed Nov. 9, 2021; Non-Final Office Action, dated Jan. 5, 2023; 27 pgs.
Nicole F.Steinmetz; U.S. Appl. No. 17/677,147, filed Feb. 22, 2022; Non-Final Office Action, dated Jan. 13, 2023; 22 pgs.
Pellico et al. (Contrast Media and Molecular Imaging. 2019; Article ID 1845637: 1-13).
Pretto et al. ("Versatile reversible cross-linking strategy to stabilize CCMV virus like particles for efficient siRNA delivery." Bioconjugate chemistry 30.12 (2019): 3069-3077).
Royston et al. (Journal of Colloidal and Interface Science. 2009; 332: 402-407).
Tamoxifen. Drug Bank Online. Website. https://go.drugbank.com/drugs/DB00675. (Accessed: Dec. 15, 2022) (Year: 2022).
Temming et al. (bioconjugate Chemistry. 2006; 17: 1385-1394).
Xiao et al. (International Journal of Molecular Medicine. 2016; 38: 1319-326).
Zhang et al. (Theranostics. 2018; 8 (9): 2521-2548).

\* cited by examiner

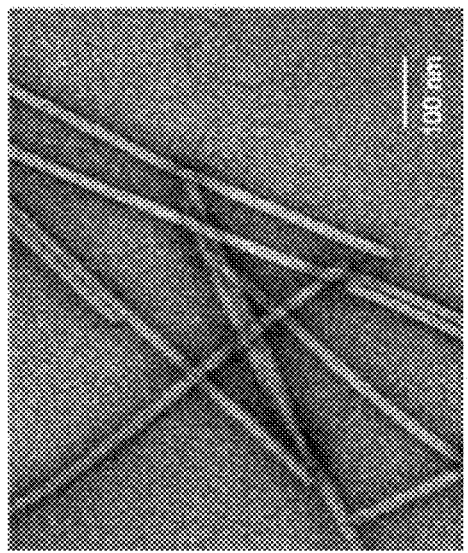
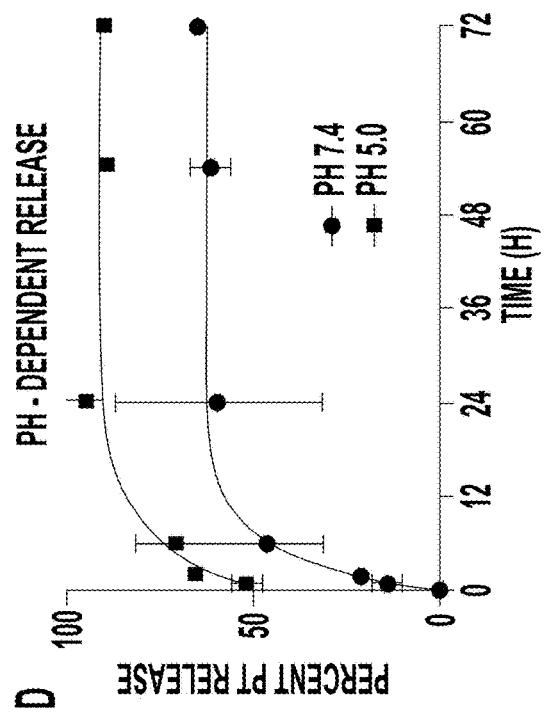
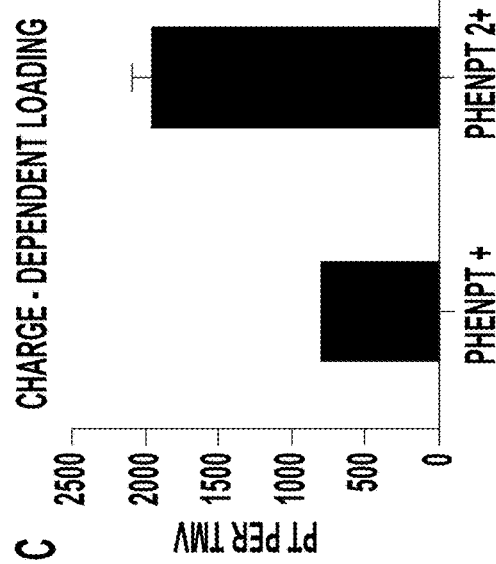
FIG. 4

A
| CELL LINE | CANCER TYPES | IC$_{50}$ in $\mu$M | | |
|---|---|---|---|---|
| | | CISPLATIN | PHENPT | PHENPT-TMV |
| MDA-MDB231 | BREAST | >20 | 3.05 | 2.21 |
| MCF-7 | BREAST | >20 | 3.59 | 2.59 |
| A2780 | OVARIAN | 0.88 | 0.56 | 0.29 |
| A2780 / DDP | OVARIAN, CISPLATIN RESISTANT | >20 | 2.05 | 1.52 |
| OV81.2 | OVARIAN, PRIMARY PATIENT CELLS | 3.58 | 0.68 | 0.67 |
| 8988T | PANCREATIC | >20 | 1.07 | 1.66 |
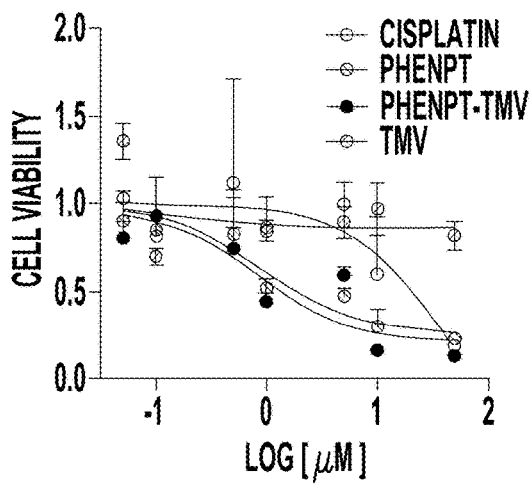
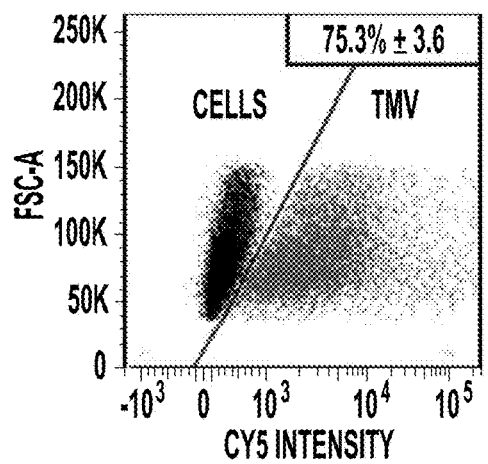
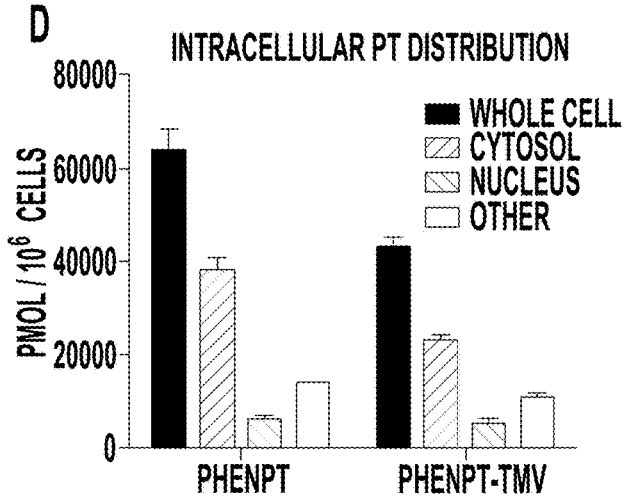
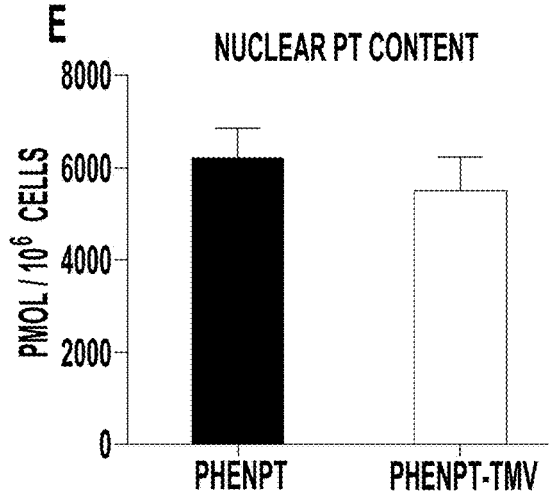
FIG. 5

ANTICANCER DRUG-CONTAINING PLANT VIRUS PARTICLES

CROSS-REFERENCE TO RELATED APPLICATIONS

This application claims priority to U.S. Provisional Application Ser. No. 62/185,881, filed on Jun. 29, 2015, and U.S. Provisional Application Ser. No. 62/201,227, filed on Aug. 5, 2015, both of which are hereby incorporated by reference in their entirety.

GOVERNMENT FUNDING

The present invention was supported by Grant No. Che 1306447, awarded by the National Science Foundation. The Government has certain rights in this invention.

BACKGROUND

Platinum-based anticancer agents play an important role in cancer therapy. The three FDA-approved Pt-drugs, cisplatin, carboplatin, and oxaliplatin, are currently in widespread clinical use in the United States. The next generation of Pt-based anticancer agents is being developed in a bid to improve the therapeutic index. One recent example, phenanthriplatin, has been developed at MIT. Despite the success of these agents in research laboratories and the clinic, toxic side effects necessitate the invention of promising drug delivery systems.

The ability of nanoparticles to carry large drug payloads and the ease with which ligands can be added so that the payload is delivered to specific target sites (e.g. cancer or cardiovascular disease) make them particularly promising for biomedical applications. The chemical composition and physical properties of nanomaterials such as shape and elasticity can significantly impact their fates in vivo. Recent studies indicate that filamentous nanomaterials have superior pharmacokinetic and tumor-homing properties. Decuzzi et al., Journal of Controlled Release 141, 320-327 (2010).

Several viral nanoparticles (VNPs) are currently being developed for nanomedical applications, where the vast majority of platforms under investigation are of spherical nature, e.g. the Human papilloma virus (HPV)-based Gardasil vaccine, Adenovirus-based gene-delivery vectors, and various plant viruses including Cowpea mosaic virus (CPMV), Brome mosaic virus (BMV), Cowpea chlorotic mottle virus (CCMV), Hibiscus chlorotic ringspot virus (HCSRV), and Red clover necrotic mottle virus (RCNMV). In contrast, few high aspect ratio VNPs have been investigated. Those that have, including Tobacco mosaic virus and bacteriophage M13, have focused mainly on in vitro tissue engineering applications. Pokorski, J. K. and N. F. Steinmetz. Mol Pharm 8 (1): 29-43 (2011).

SUMMARY

The inventors have investigated the use of plant virus-based nanoparticles (VNPs) for targeted drug delivery of anticancer agents, such as platinum based anticancer agents. They have developed two different approaches to achieve this goal. One is to non-covalently encapsulate cationic anticancer agents within the anionic channel of tobacco mosaic virus (TMV). FIG. 1 indicates how phenanthriplatin is being encapsulated within TMV. The second approach involves covalently conjugating cisplatin derivatives to the interior cavity of the icosahedral cowpea mosaic virus (CPMV), or to the interior channel of TMV. As shown in FIG. 2, the covalent conjugation can be achieved through reaction of either the glutamic acid residue from the virus and the amino group from the cisplatin prodrug, or the cysteine of the virus and the maleimide of the Pt species. In some embodiments, the exterior surfaces of the nanoparticle carriers can be modified with stealth coatings (e.g. PEG) for improved bioavailability and/or targeting ligands (e.g. arginylglycylaspartic acid (RGD), a tripeptide commonly used in medical research for tumor-targeting). Data indicate that upon entering cancer cells, the anticancer drugs will be released after enzymatic digestion of the nanoparticles. In vitro and in vivo efficacy were evaluated in tissue culture and xenograft models.

This newly designed delivery system represents a first-time investigation into the application of virus-based nanoparticles for drug delivery of platinum-based anticancer agents. The inventors have shown that these plant viruses (including but not limited to TMV and CPMV) have several advantages when used for biomedical applications, including low toxicity, high blood compatibility, and tumor specificity. Loaded within such vehicles, Pt anticancer agents will be able to reach tumors more efficiently, resulting in minimized damage to healthy tissue.

BRIEF DESCRIPTION OF THE FIGURES

The present invention may be more readily understood by reference to the following drawings.

FIGS. 4A-D characterize PhenPt-TMV. (FIG. 4A) TEM images of negative-stained PhenPt-TMV coated grids. (FIG. 4B) Hydrodynamic diameter (DH) measured by dynamic light scattering and zeta potential (ζ) of TMV and PhenPt-TMV. (FIG. 4C) Platinum content per TMV after encapsulation of phenanthriplatin and its aquated form measured by ICP-MS. (FIG. 4D) Percent phenanthriplatin release from TMV over time in PBS at 7.4 (blue) and acetate buffer at 5.0 (red)

FIGS. 5A-E show cellular uptake and efficacy of PhenPt-TMV in vitro. (FIG. 5A) IC$_{50}$ values for cisplatin, free phenanthriplatin (PhenPt), and PhenPt-TMV in a six-cell line panel as determined by MTT assays. (FIG. 5B) MTT assay using MDA-MB-231 cells. (FIG. 5C) Flow cytometry of MDA-MB-231 cells without treatment and following 3 h incubation with Cy5-labeled TMV. (FIGS. 5D-E) Intracellular distribution and nuclear content of platinum in A2780 cells following 24-h incubation with free phenanthriplatin and PhenPt-TMV.

(FIG. 6A) Composite image of TMV in MDA-MB-231 cells at 8 h post incubation. TMV is shown in green (immunostained using rabbit anti-TMV) (FIG. 6B), nuclei in blue (stained with DAPI), and endolysosomes in red (stained with Lamp-1) (FIG. 6C). (FIG. 6D) Colocalization analysis using the "co-localization highlight" plug-in and ImageJ software. White=co-localization of TMV and Lamp-1.

(FIG. 7A) cisplatin vs phenanthriplatin, (FIG. 7B) PhenPt-TMV vs TMV, and (FIG. 7C) PhenPt-TMV vs phenanthriplatin.

(FIG. 9A) Representative Maestro imaging of excised organs 24 h after administration Cy5-labeled PhenPt-TMV. (FIG. 9B) Quantitative ROI analysis of excised organs from (FIG. 9A) quantifying average fluorescence intensity (tissues from n=3 animals were analyzed). (FIGS. 9C-D) Platinum concentration in organ tissue as measured by atomic absorption spectroscopy 24 h post-administration of phenanthriplatin or PhenPt-TMV followed by tissue homogenization.

(FIG. 10A) Weight of treated tumor bearing mice over the course of the study. (FIG. 10B) AST and ALT liver enzyme testing 24 h following administration of PBS, TMV, phenanthriplatin, or PhenPt-TMV. (FIG. 10C) H&E stained liver and kidney tissue from mice 24 h following administration of PBS, TMV, phenanthriplatin, or PhenPt-TMV.

DETAILED DESCRIPTION

Figure 1:
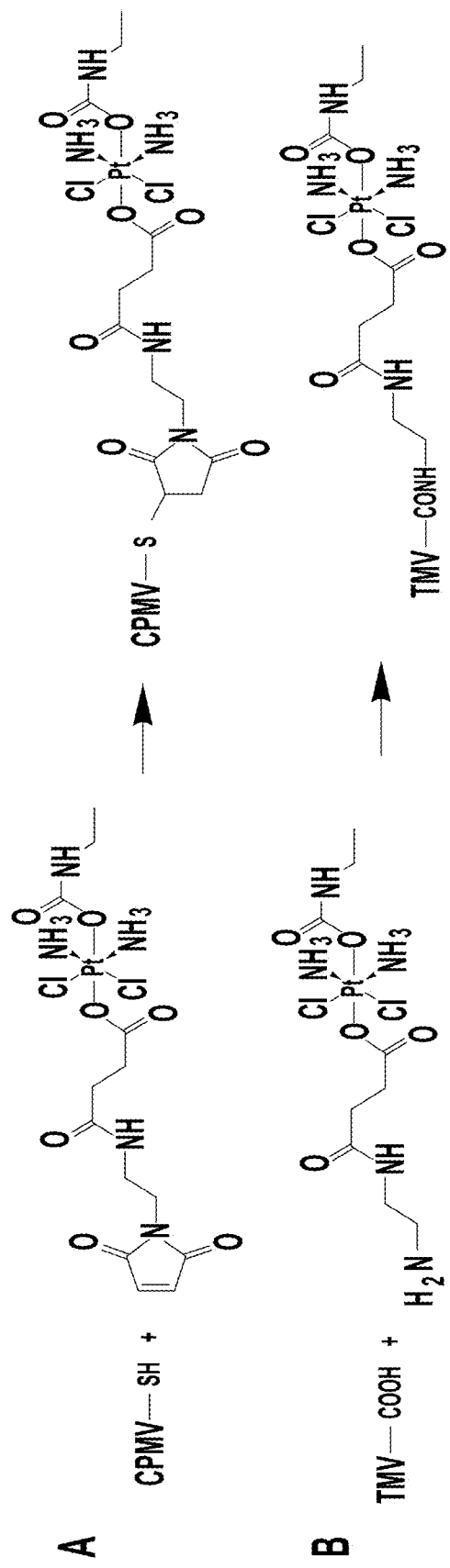
FIGS. 1A-B are a schematic illustration showing a scheme for the covalent conjugation of cisplatin prodrugs to cowpea mosaic virus (CPMV) (FIG. 1A) and tobacco mosaic virus (TMV) (FIG. 1B).

The present invention provides anticancer virus particles that are filamentous or rod-shaped plant virus particle containing an anticancer agent within the interior of the virus particle. The anticancer agent can be attached either covalently or non-covalently within the interior of the virus particle. In some aspects of the invention, a therapeutically effective amount of an anticancer virus particle can be administered to a subject identified as having cancer to provide a method of cancer treatment.

Definitions

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural references unless the content clearly dictates otherwise. Thus, for example, reference to "a virus particle" includes a combination of two or more virus particles, and the like.

The term "about" as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

Prevention, as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or as a result of family history.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Targeting," as used herein, refers to the ability of filamentous plant virus particles to be delivered to and preferentially accumulate in cancer tissue in a subject.

In one aspect, the invention provides an anticancer virus particle, comprising a filamentous or rod-shaped plant virus particle containing an anticancer agent within the interior of the virus particle. Providing anticancer virus particles with anticancer agent within the virus particles helps protect the anticancer agents from degradation while in the bloodstream, while allowing their release upon degradation of the virus particles within cancer cells.

Filamentous and Rod-shaped Plant Viruses

A filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm. Filament-like virus particles are flexible in addition to being long and thin, and therefore some embodiments of the invention are directed to use of a flexible filamentous plant virus. Use of filamentous plant viruses provides the advantages of improved tumor targeting and penetration. Embodiments of the invention can deliver about 10%, about 20%, about 30%, about 40%, or even about 50% or more of the injected dose to tumor tissue.

In some embodiments, the filamentous plant virus belongs to a specific virus family, genus, or species. For example, in some embodiments, the filamentous plant virus belongs to the Alphaflexiviridae family. The Alphaflexiviridae family includes the genus *Allexivirus, Botrexvirus, Lolavirus, Mandarivirus, Potexvirus,* and *Sclerodarnavirus.* In some embodiments, the filamentous plant virus belongs to the genus *Potexvirus.* In further embodiments, the filamentous plant virus belongs to the Potato Virus X species.

A rod-shaped plant virus is a virus that primarily infects plants, is non-enveloped, and is shaped as a rigid helical rod with a helical symmetry. Rod shaped viruses also include a central canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, in some embodiments, the rod-shaped plant virus belongs to the Virgaviridae family. The Virgaviridae family includes the genus *Furovirus, Hordevirus, Pecluvirus, Pomovirus, Tobamovirus,* and *Tobravirus.* In some embodiments, the rod-shaped plant virus belongs to the genus *Tobamovirus.* In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are ~300 nm in length and ~18 nm in diameter. Negatively stained electron microphotographs show a distinct inner channel of ~4 nm.

Filamentous and rod-shaped plant virus particles have an interior and an exterior. The exterior of a plant virus particle is the portion of the virus particle that is directly exposed to the environment. The interior of the plant virus particle is the portion of the virus particle that typically is adjacent to the genomic material within the virus particle, and is not directly exposed to the environment.

Cytotoxic Compounds

The invention makes use of filamentous or rod-shaped plant virus particles containing an anticancer agent within the interior of the virus particle, also referred to herein as anticancer virus particles. Anticancer agents are compounds that have a cytostatic or cytotoxic effect on cancer cells. Suitable anticancer agents include radioactive agents or isotopes (radionuclides), chemotoxic agents such as differentiation inducers, inhibitors, a wide variety of small molecule chemotoxic drugs, toxin proteins and derivatives thereof, as well as nucleotide sequences (or their antisense sequence).

Preferred radionuclides for use as anticancer agents are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$Bi can be conjugated to filamentous or rod-shaped viral particles for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodo-3-pyridinecarboxylate (SIPC). Any iodine isotope can be utilized in the recited iodo-reagents. Other radionuclides can be conjugated to the filamentous or rod-shaped plant virus particles by suitable chelation agents known to those of skill in the nuclear medicine arts.

Preferred toxin proteins for use as anticancer agents include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents can elicit undesirable immune responses in the patient, especially if injected intravascularly, it is advantageous to position them within the filamentous or rod-shaped plant virus particles.

Anticancer agents include a large number of small-molecule antitumor agents. Examples of antitumor agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, phenanthriplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives thereof.

In some embodiments, the anticancer agent is a cationic anticancer agent that is non-covalently encapsulated in the interior of the plant virus particle. Encapsulating cationic anticancer agents is facilitated by the presence of an anionic channel within the interior of the virus particle. Cationic anticancer agents can be readily identified by those skilled in the art.

In further embodiments, the anticancer agent is a platinum-based anticancer agent. Platinum-based anticancer agents include both neutral (platinum(II)) and cationic (platinum(IV)) platinum-based anticancer agents. Examples of neutral platinum-based anticancer agents include cisplatin, carboplatin, oxaliplatin, nedaplatin, and lobaplatin, which are in a sense more traditional platinum-based anticancer compounds. Cationic platinum-based anticancer agents include a variety of compounds such as satraplatin, picoplatin, and phenanthriplatin. For additional platinum(IV) anticancer agents, see Lovejoy, K, and Lippard, S., Dalton Trans. 48, 10651-10659 (2009) and Zheng et al., JACS, 136, 8790-8798 (2014), the disclosures of which are incorporated herein by reference.

Association of Anticancer Agents with the Plant Virus Particles

Figure 3:
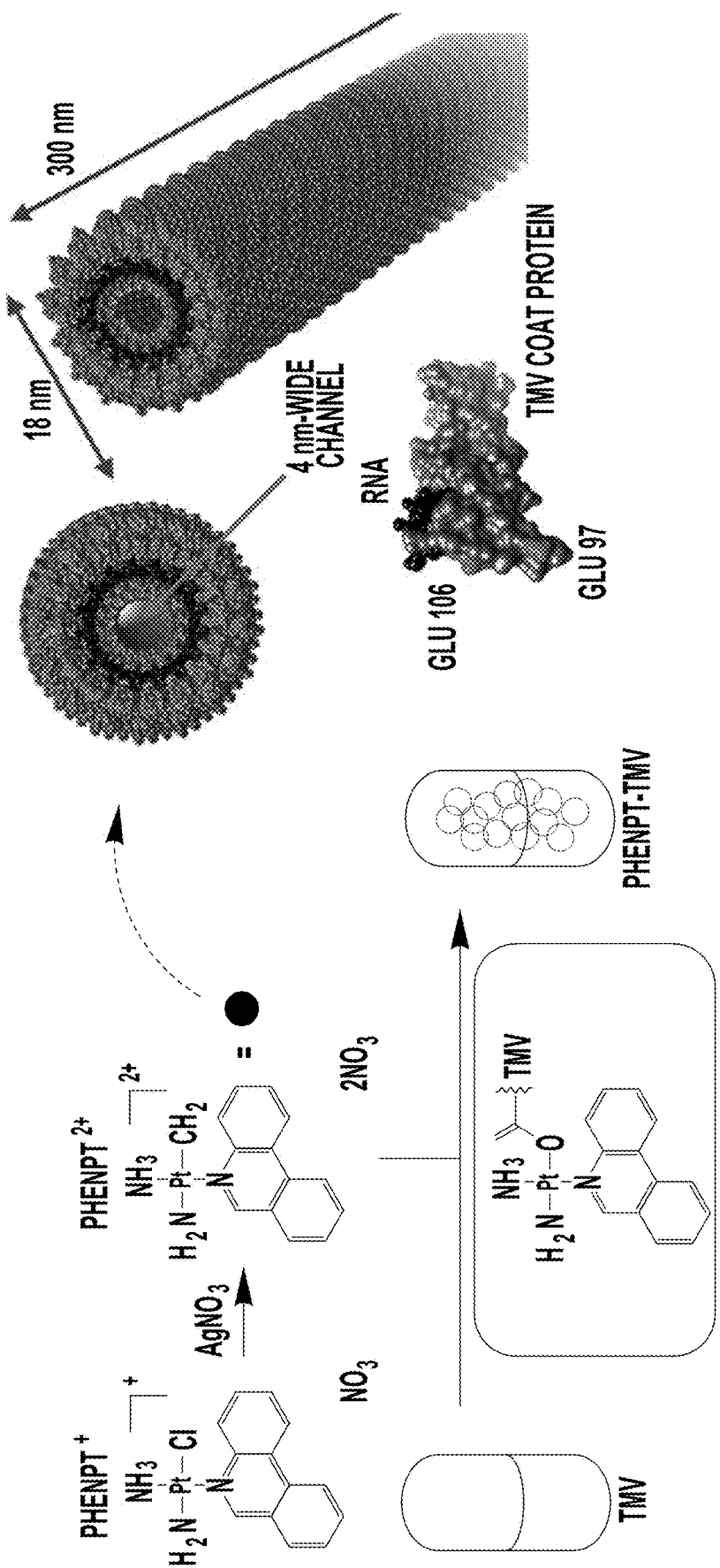
FIG. 3 is a schematic illustration showing a loading scheme and structures of phenanthriplatin and PhenPt-TMV, where PhenPt-TMV is prepared by nanoencapsulation of PhenPt$^{2+}$ within the virus. Structure of tobacco mosaic virus (TMV, images were created using Chimera software and PDB entry TMV2); the TMV coat protein and assembled hollow nanotube are shown in cross-sectional and longitudinal orientations. The coat protein is depicted in gray, the RNA in black, and interior glutamic acids Glu 97 and Glu 106 are highlighted in red.
Figure 6:
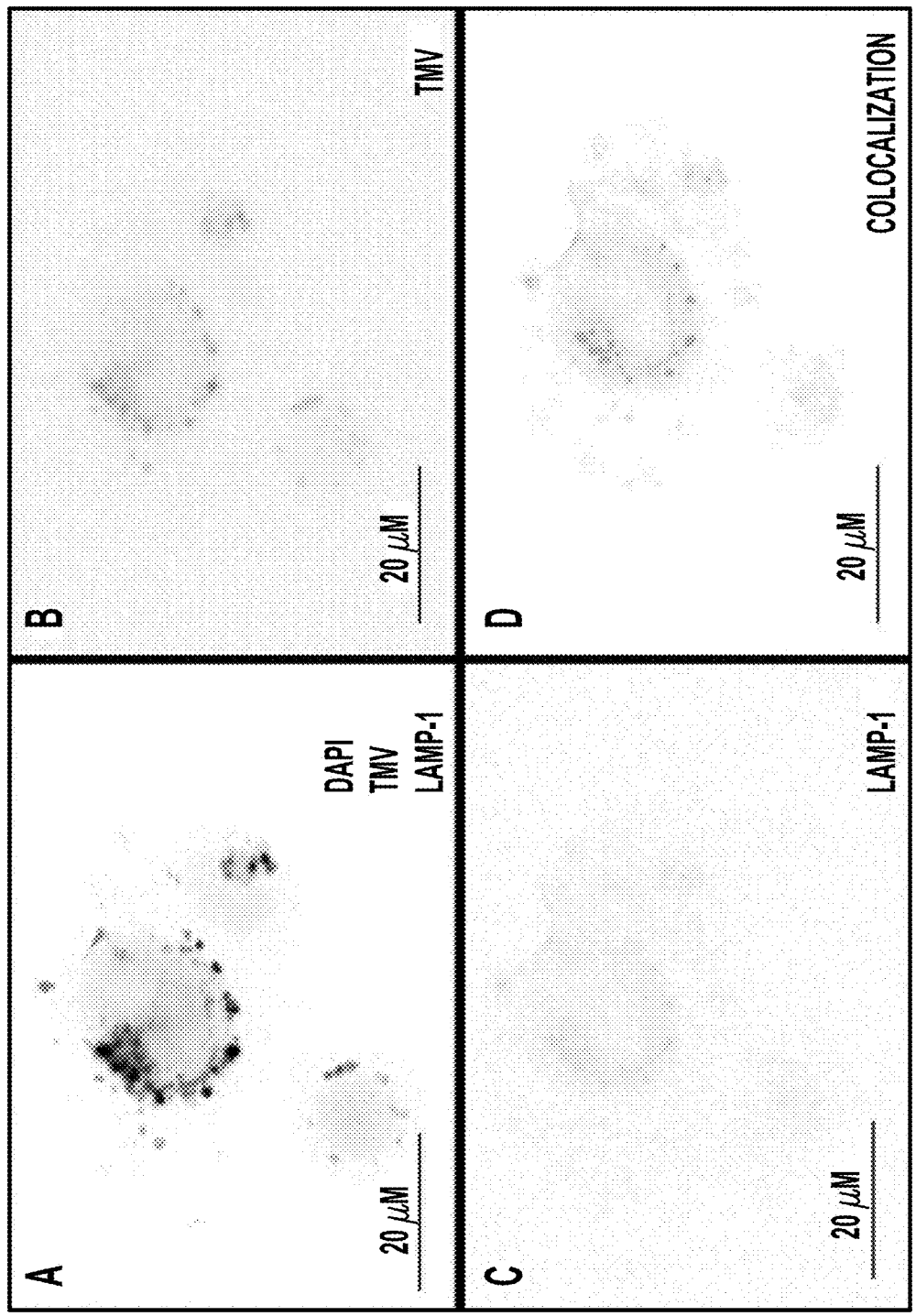
FIGS. 6A-D show cellular trafficking of TMV within MDA-MB-231 cells.

The anticancer agent is contained within the interior of the filamentous or rod-shaped plant virus particle. Preferably, the anticancer agent is found solely in the interior, with little or no anticancer agent associating with the exterior of the virus particle. In some embodiments, the anticancer agent is a cationic anticancer agent that is non-covalently encapsulated in the interior of the plant virus particle, as shown in FIG. 3, while in other embodiments the anticancer agent is covalently conjugated to the interior of the plant virus particle, using, for example, the linking chemistry shown in FIGS. 1A-B. Cationic anticancer agents can be loaded into the plant virus particles using an electrostatically-driven process through interaction of the positively charged drug with the negatively-charged interior protein surface of the hollow virus structure. The anticancer agent can be associated with the interior of the virus particle either as a result for an affinity to an interior structure such as a channel within the interior of the virus particle, or by linkage through groups only expressed on the interior of the virus particle.

In general, anticancer agents can be conjugated to the filamentous or rod-shaped plant virus particles by any suitable technique, with appropriate consideration of the need for pharmacokinetic stability and reduced overall toxicity to the patient. The term "conjugating" when made in reference to an anticancer agent and a filamentous plant virus particle as used herein means covalently linking the agent to the virus subject to the single limitation that the nature and size of the agent and the site at which it is covalently linked to the virus particle do not interfere with the biodistribution of the modified virus.

An agent can be coupled to a filamentous or rod-shaped plant virus particle either directly or indirectly (e.g. via a linker group). In some embodiments, the agent is directly attached to a functional group capable of reacting with the agent. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). In addition, genetic modification can be applied to introduce any desired functional residue, including non-natural amino acids, e.g. alkyne- or azide-functional groups. See Pokorski, J. K. and N. F. Steinmetz Mol Pharm 8 (1): 29-43 (2011).

Alternatively, a suitable chemical linker group can be used. A linker group can serve to increase the chemical reactivity of a substituent on either the agent or the virus particle, and thus increase the coupling efficiency. Preferred groups suitable for attaching agents to virus particles are lysine residues present in the viral coat protein.

Suitable linkage chemistries include maleimidyl linkers and alkyl halide linkers and succinimidyl (e.g., N-hydroxysuccinimidyl (NHS)) linkers (which react with a primary amine on the filamentous or rod-shaped plant virus particle). Several primary amine and sulfhydryl groups are present on viral coat proteins, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be affected, for example, through amino groups, carboxyl groups, sulfhydryl groups or oxidized carbohydrate residues.

In some embodiments, for example where an anticancer agent is more potent when free from the anticancer virus particle of the present invention, it can be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710); by irradiation of a photolabile bond (e.g., U.S. Pat. No. 4,625,014); by hydrolysis of derivatized amino acid side chains (e.g., U.S. Pat. No. 4,638,045); by serum complement-mediated hydrolysis (e.g., U.S. Pat. No. 4,671,958); and acid-catalyzed hydrolysis (e.g., U.S. Pat. No. 4,569,789).

It can be desirable to couple more than one type of anticancer agent within a filamentous or rod-shaped plant virus particle of the invention. By poly-derivatizing the plant viral particle of the invention, several cytotoxic strategies can be simultaneously implemented. For example, more than one type of anticancer agent can be coupled to a filamentous or rod-shaped plant virus particle.

Cancer Treatment

Another aspect of the invention provides a method of treating cancer in a subject identified as having cancer by administering to the subject a therapeutically effective amount of an anticancer virus particle, comprising a filamentous or rod-shaped plant virus particle containing an anticancer agent within the interior of the virus particle. The anticancer virus particle can have any of the features described herein. For example, platinum-based anticancer agents can be used, and if the anticancer agent is a cationic anticancer agent, it may be non-covalently encapsulated in the interior of the plant virus particle, while in other embodiments the anticancer agent is covalently conjugated to the interior of the plant virus particle.

Filamentous or rod-shaped plant virus particles including anticancer agents can be used to treat a variety of different types of cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the filamentous or rod-shaped plant virus particles including anticancer agents are used to treat or image cancer tissue selected from the group consisting of ovarian cancer, colon cancer, brain cancer, or breast cancer.

The filamentous plant virus is used to target cancer tissue in a subject. As used herein, targeting cancer tissue includes the ability of the anticancer virus particles to reach and preferably accumulate within cancer tissue after being administered to the subject. The ability of filamentous plant virus particles to target cancer tissue is supported by the biodistribution studies carried out by the inventors. See International Patent Publication WO/2013/181557. The disclosure of which is incorporated herein by reference. While not intending to be bound by theory, it currently appears that filamentous plant virus particles are taken up by blood components such as macrophage cells of the immune system, which subsequently accumulate in tumor tissue, thereby delivering the filamentous plant virus to the tumor cells.

Figure 2:
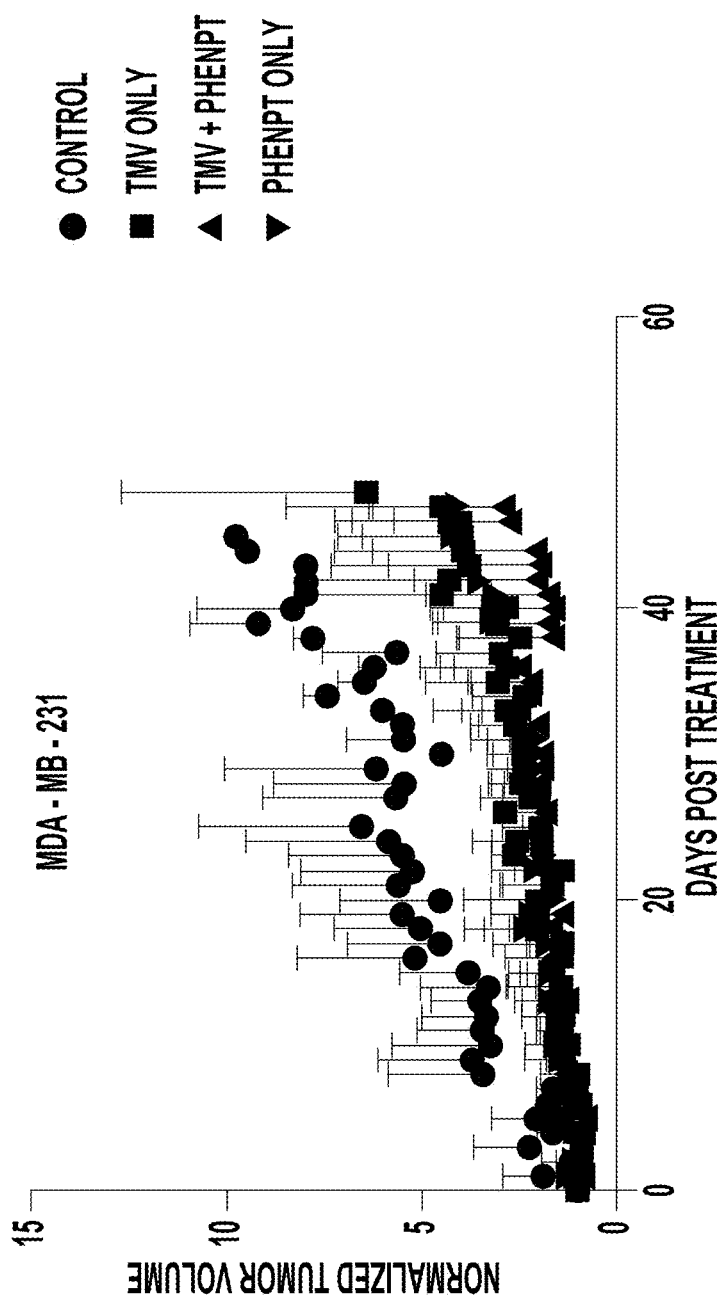
FIG. 2 is a graph comparing the antitumor activity of TMV only with TMV including phenanthriplatin and phenthriplatin alone.

In some embodiments, the virus particle can provide additional anticancer activity. While not intending to be bound by theory, this additional anticancer therapy appears to be the result of an immunotherapeutic effect of the virus particles. The combined anticancer effect of the virus particles bearing phenanthriplatin is shown in FIG. 2. As can be seen in FIG. 2, TMV particles have anticancer activity even in the absence of phenanthriplatin, but show the highest activity when TMV particles bearing phenanthriplatin are used.

Targeting Moieties

In some embodiments, a targeting moiety can also be attached to the filamentous or rod-shaped plant virus particle. By "targeting moiety" herein is meant a functional group which serves to target or direct the virus particle to a particular location, cell type, diseased tissue, or association. In general, the targeting moiety is directed against a target molecule. Thus, for example, antibodies, cell surface receptor ligands and hormones, lipids, sugars and dextrans, alcohols, bile acids, fatty acids, amino acids, peptides and nucleic acids may all be attached to localize or target the anticancer virus particle to a particular site. In some embodiments, the targeting moiety allows targeting of the plant virus particles of the invention to a particular tissue or the surface of a cell. Preferably, the targeting moiety is linked to the exterior surface of the virus to provide easier access to the target molecule.

In some embodiments, the targeting moiety is a peptide. For example, chemotactic peptides have been used to image tissue injury and inflammation, particularly by bacterial infection; see WO 97/14443, hereby expressly incorporated by reference in its entirety. Another example, are peptides specific to fibrin or vascular cell adhesion molecules to direct the imaging probe to sites of inflammation, such as an atherosclerotic plaque. In other embodiments, the targeting moiety is an antibody. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin.

In some embodiments, the antibody is directed against a cell-surface marker on a cancer cell; that is, the target molecule is a cell surface molecule. As is known in the art, there are a wide variety of antibodies known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

Coatings on the Virus Particle Exterior

In some embodiments, a coating can be added to the exterior of the plant virus particle to improve bioavailability. Administering an anticancer virus particle to a subject can sometimes generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Generation of an immune response by the anticancer virus particles is typically undesirable. Accordingly, in some embodiments it may be preferable to modify the exterior of the plant virus particle or take other steps to decrease the immune response. For example, an immunosuppressant compound can be administered to decrease the immune response. More preferably, the anticancer virus particle can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of the anticancer virus particle is decreased by PEGylation. PEGylation is the process of covalent attachment of polyethylene glycol (PEG) polymer chains to a molecule such as a filamentous plant virus carrier. PEGylation can be achieved by incubation of a reactive derivative of PEG with the plant virus particle exterior. The covalent attachment of PEG to the anticancer virus particle can "mask" the agent from the host's immune system, and reduce production of antibodies against the carrier. PEGylation also may provide other benefits. PEGylation can be used to vary the circulation time of the filamentous plant virus carrier. For example, use of PEG 5,000 can provide an anticancer virus particle with a circulation half-life of about 12.5 minutes, while use of PEG 20,000 can provide an anticancer virus particle with a circulation half life of about 110 minutes.

The first step of PEGylation is providing suitable functionalization of the PEG polymer at one or both terminal positions of the polymer. The chemically active or activated derivatives of the PEG polymer are prepared to attach the PEG to the anticancer virus particle. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

Administration and Formulation of Anticancer Plant Virus Particles

In some embodiments, the anticancer virus particle is administered together with a pharmaceutically acceptable carrier to provide a pharmaceutical formulation. Pharmaceutically acceptable carriers enable the anticancer virus particle to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the anticancer virus particle into association with a pharmaceutically acceptable carrier that constitutes one or more accessory ingredients. In general, the formulations are prepared by uniformly and intimately bringing the anticancer virus particle into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated anticancer virus particle can be administered as a single dose or in multiple doses.

Useful dosages of the anticancer agents and anticancer virus particles can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the anticancer virus particles vary depending upon many different factors, including means of administration, target site, physiological state of the patient, whether the patient is human or an animal, other medications administered, and whether treatment is prophylactic or therapeutic.

For administration of the anticancer virus particles for cancer treatment in a mammalian subject or an avian subject, the dosage of the anticancer agent ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. A suitable amount of anticancer virus particle is used to provide the desired dosage. An exemplary treatment regime entails administration once per every two weeks or once a month or once every 3 to 6 months. The anticancer virus particle is usually administered on multiple occasions. Alternatively, the anticancer virus particle can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The following example is for the purpose of illustration only and is not intended to limit the scope of the claims, which are appended hereto.

EXAMPLE

Materials and Methods

Synthesis of PhenPt-TMV

Established protocols were used to produce TMV in Nicotiana benthamiana plants (Bruckman, M. A.; Steinmetz, N. F. Chemical Methods Mol. Biol. 2014, 1108, 173-185) and synthesize phenanthriplatin. (Park, G. Y.; Wilson, J. J.; Song, Y.; Lippard, S. J. Phenanthriplatin, Proc. Natl. Acad. Sci. U.S.A. 2012, 109, 11987-11992). Phenanthriplatin was allowed to react with $AgNO_3$ to give the aquated species (FIG. 3), which was then mixed with TMV using a 17,000-fold excess of aquated phenanthriplatin in 10 mM potassium phosphate buffer pH 7.8. Protein concentration was kept at 1 mg/mL, and the reaction was stopped after 30 min. The PhenPt-TMV complex was purified over a 40% (w/v) sucrose cushion at 160,000 g for 3 h and resuspended in sterile PBS. The concentration of TMV was determined by UV-vis spectroscopy, (Bruckman, M. A.; Steinmetz, N. F. Chemical Methods Mol. Biol. 2014, 1108, 173-185) and the platinum content was measured using ICP-MS. Structural integrity was confirmed by transmission electron microscopy, dynamic light scattering, and zeta potential measurement.

Cell Uptake and Cytotoxicity

Cell uptake was monitored by using MDA-MB-231 cells, a generous gift from Dr. Schiemann, Case Western Reserve University, and sulfo-Cy5 fluorescently labeled TMV and flow cytometry methods were as previously described. (Shukla, S.; Eber, F. J.; Nagarajan, A. S.; DiFranco, N. A; Schmidt, N.; Wen, A. M.; Eiben, S.; Twyman, R. M.; Wege, C.; Steinmetz, N. F. Adv. Healthcare Mater. 2015, 4, 874-882). Data were recorded with a BD LSRII flow cytometer and analyzed using FlowJo 8.63 software. The intracellular distribution of phenanthriplatin and PhenPt-TMV was determined following a 24 h incubation with A2780 cells. Cell components were separated by using a commercially available kit (Thermo Scientific NE-PER Nuclear and CytoplasmicExtraction Kit) and atomic absorption spectroscopy as previously described. Efficacy was analyzed by using the MTT assay (ATCC) and a panel of human cancer cell lines: A2780 (ovarian cancer), A2780/CP70 (ovarian cancer resistant to cisplatin), OV81.2 (ovarian cancer, primary patient cells; cells were a generous gift from Dr. DiFeo, Case Western Reserve University), 8988T (pancreatic 375 cancer) cells were a generous gift from Dr. Ghoroghchian, MIT. LNCAP (prostate cancer), MCF-7 (breast cancer), MDA-MB231 (breast cancer) cells were obtained from ATCC unless indicated otherwise. The assay was performed as per manufacturer's recommendation; a BioTek Synergy HT multidetection microplate reader was used for read-out.

Intracellular Trafficking

Intracellular trafficking was monitored in MDA-MB-231 cells; 25,000 cells were seeded overnight on glass coverslips and incubated for 8 h with $1\times10^6$ TMV particles per cell. Following incubation, cells were washed, fixed, and stained. Cell membrane was stained using wheat germ agglutinin conjugated to AlexaFluor 555. TMV was stained using a rabbit anti-TMV antibody primary and a goat antirabbit secondary conjugated to AlexaFluor 647. Endolysosomes were stained using a mouse antihuman Lamp-1 antibody primary and a goat antimouse secondary conjugated to AlexaFluor 488. Slides were imaged using Zeiss Axio Imager Z1 fluorescent inverted high-resolution microscope with motorized stage.

In Vivo Phenanthriplatin Delivery Using the MDA-MB-231 Model

All animal studies were carried using IACUC-approved procedures. NCR nu/nu mice were injected subcutaneously into the right flank using $2\times10^6$ MDA-MB-231 cells suspended in 100 µL of media and Matrigel (Corning) at a 1:1 ratio. Once established, tumors were monitored daily, and treatment was started when tumors reached 250-300 $mm^3$. Two independent studies with n=5 animals per groups were performed. Treatment was administered intravenously at weekly intervals at a dosage of 1.0 mg/kg body weight phenanthriplatin. Groups were treated with phenanthriplatin, PhenPt-TMV, TMV, cisplatin, and PBS. PhenPt-TMV was prepared fresh, and platinum content was determined immediately prior to every injection. The dosage was normalized to platinum or TMV content. Tumors were measured daily and total volume was calculated using the formula: $v=[l\times w^2]/2$. Mice were weighed every other day to monitor potential side effects. Mice were euthanized following 30 days of treatment or as determined by IACUC guidelines. Hematoxylin and eosin staining was performed according to previously described methods (Fischer, A. H.; Jacobson, K. A.; Rose, J.; Zeller, R. Cold Spring Harbor Protoc. 2008, 2008, pdb.prot4986) and imaged using Zeiss Axio Imager Z1 fluorescent inverted high resolution microscope with motorized stage.

Biodistribution

Cy5-labeled PhenPt-TMV and free PhenPt (at 1.0 mg/kg) were administered intravenously into MDA-MB-231 tumor bearing mice. Mice were euthanized after 24 h and imaged using the Maestro fluorescence imaging system. Organs were removed and imaged individually and ROIs were evaluated. Platinum content in each organ was extracted and determined using graphite furnace atomic absorption spectroscopy (GFAAS).

Liver and Kidney Toxicity

Balb/c mice (n=3) were injected with 100 µL PBS, TMV, phenanthriplatin, or PhenPt-TMV at the same dosage administered for the efficacy studies (normalized to 1.0 mg/kg body weight phenanthriplatin). After 24 h, blood was collected via retro-orbital bleeds and tested for ALT and AST activity levels using commercially available kits (Sigma-Aldrich). Animals were then euthanized, and livers and kidneys were paraffin-embedded, sectioned, and stained as described above.

Results and Discussion

Synthesis and Characterization of TMV-encapsulated Phenanthriplatin

TMV was propagated and purified from Nicotiana benthamiana plants at yields of around 10 mg per gram infected leaf tissue; methods are as previously reported. Phenanthriplatin was synthesized as described previously.

Each TMV nanorod consists of 2130 identical copies of a coat protein unit arranged helically around a single-stranded RNA molecule, creating an accessible 4 nm-wide central channel (FIG. 3). TMV has served as a model system in plant pathology and structural biology since the early 1900s; its structure is well-defined. The protein-based scaffold provides a template that enables highly precise insertion of guest molecules through region-specific targeting of solvent-exposed surface groups. Bioconjugate chemistry targeting internal glutamic acids and external tyrosine residues is well established, and carbodiimide, diazonium, and N-hydroxysuccinimide reagents can be used to introduce alkyne or benzaldehyde ligands for subsequent derivatization using Cu(I)-catalyzed azide-alkyne cycloaddition, hydrazone coupling, or oxime condensation. We previously showed that covalent strategies enable incorporation of contrast agents and/or peptide ligands. However, these methods involve multiple synthetic steps requiring repeated purification from excess reagents, thereby lowering the yield of the final product. These technical challenges were not an issue in the present example, where nano-encapsulation of the cationic guest in the anionic tubular environment of the virus afforded the desired phenanthriplatin-loaded TMV formulation (PhenPt-TMV).

The inner and outer surfaces of TMV provide distinct chemical environments. The interior channel affords a high density of negative surface charges from the 4260 glutamic acids (Glu 97 and 106, see FIG. 3), whereas no carboxylates are present on the exterior TMV surface.

To test whether the association of phenanthriplatin and TMV was electrostatically driven, both phenanthriplatin (PhenPt$^+$, FIG. 3) and its aquated form, (PhenPt$^{2+}$, FIG. 3), obtained through reaction with AgNO$_3$, were allowed to react with TMV by mixing in solution. Following purification of PhenPt-TMV using ultracentrifugation to remove excess reagents, the Pt content per TMV particle was determined by inductively coupled plasma mass spectroscopy (ICP-MS). The results indicate that a 30-min loading with 2000±200 phenanthriplatin cations per TMV when using PhenPt2$^+$, supporting the conclusion that binding occurs to the carboxylate groups lining the inner core of the virus (FIG. 4C). The 2+ charge of PhenPt$^{2+}$ compensates two carboxylate amino acid side chains lining the interior surface of the virus. PhenPt$^+$ resulted in fewer than 1000 phenanthriplatin cations per nanorod.

To confirm that phenanthriplatin loading requires the internal carboxylates, we conjugated the positively charged cyanine5 dye (Cy5) to the interior carboxylates using a combination of carbodiimide coupling to introduce an alkyne followed by Cu(I)-catalyzed azide-alkyne cycloaddition of an azide-functional Cy5 ("click" chemistry). The reactions and Cy5-TMV particle characterization were performed as previously described. Attempted phenanthriplatin loading of the Cy5-modified TMV did not yield any detectable encapsulation as measured by ICP-MS, supporting exclusively interior loading through electrostatic gating and, most likely, coordination of the carboxylates to platinum atoms.

Transmission electron microscopy (TEM) imaging of PhenPt-TMV confirms that the nanorods remain structurally sound after phenanthriplatin loading (FIG. 4A). Dynamic light scattering and zeta potential measurements indicate no statistically significant differences comparing native TMV and PhenPt-TMV, further supporting interior loading of the compound (FIG. 4B).

Next, we evaluated the phenanthriplatin release profile. PhenPt-TMV was prepared as described and dialyzed against PBS at pH 7.4 or sodium acetate buffer at pH 5.0. These conditions were chosen to mimic the acidic lysosomal and tumor microenvironments compared to physiological pH in blood. Increased release rates were apparent at low pH in solutions of PhenPt-TMV formulations. Approximately half the phenanthriplatin content was released within the first hour, release of the remaining cation occurred at 24 h. In stark contrast, release at pH 7.4 was significantly slower. About 50-60% of the phenanthriplatin content was released after 24 h reaching a plateau, and complete release was not observed over the 72 h time course. Although the PhenPt-TMV complex lacks long-term stability, the one-step loading process facilitates its formation immediately prior to use.

The rapid release of phenanthriplatin in acidic environments may be explained by protonation of the carboxylic acids, which destabilizes the PhenPt-TMV complex. This finding is important considering that previous approaches to drug delivery of platinum compounds failed in the clinic owing to lack of drug release, an example being trials evaluating liposomal formulations of cisplatin (SPI-77). Our data indicate that the virally encapsulated materials efficiently release their cargo; at the same time, stability at physiological pH is expected to protect against premature release while in circulation, thereby preventing off-target systemic effects.

PhenPt-TMV Cytotoxicity and Cell Interactions In Vitro

The anticancer activity of PhenPt-TMV was evaluated using a panel of cancer cells and compared to those of unencapsulated phenanthriplatin and cisplatin. The data indicate that PhenPt-TMV maintained efficacy compared to free phenanthriplatin. Both PhenPt-TMV and phenanthriplatin outperformed cisplatin in cancer cell lines of breast, ovarian, and pancreatic origin (FIGS. 5A-B). Whereas the IC$_{50}$ values for cisplatin ranged from 0.88 μM to >20 μM, the IC50 values for phenanthriplatin and PhenPt-TMV ranged from 0.29 to 3.59 μM, depending on cell type. Free phenanthriplatin and PhenPt-TMV showed enhanced efficacy in ovarian cancer cells resistant to cisplatin treatment. Enhanced efficacy was also observed using primary patient cells OV81.2. Native TMV showed no cytotoxicity (FIG. 5B), attesting to its biocompatibility.

Next, we determined cell interactions and the intracellular distribution of PhenPt comparing free and TMV-delivered material (FIGS. 5C-E). Using MDA-MB-231 cells and flow cytometry protocols, we determined that TMV efficiently interacts with cancer cells (FIG. 5C). This result is consistent with TMV cellular trafficking experiments (FIGS. 6A-D) and previous reports that TMV is internalized by cancer cells through endocytosis and targeted to the endolysosome, where the free drug is released following degradation of the proteinaceous carrier. Assessment of the intracellular distribution of platinum content revealed that 24 h after exposure of A2780 cells to PhenPt-TMV phenanthriplatin was detected in the nucleus at levels comparable to those obtained with free phenanthriplatin (FIGS. 5D-E). These results are consistent with PhenPt-TMV release from the virus intra-cellularly, where the carboxylic acids become protonate leading to phenanthriplatin release (see FIG. 4D). Following initial release, the acidic environment and the presence of hydrolases and proteases will degrade the proteinaceous carrier over time, further releasing membrane permeable phenanthriplatin.

PhenPt-TMV In Vivo Efficacy and Biodistribution

Figure 7:
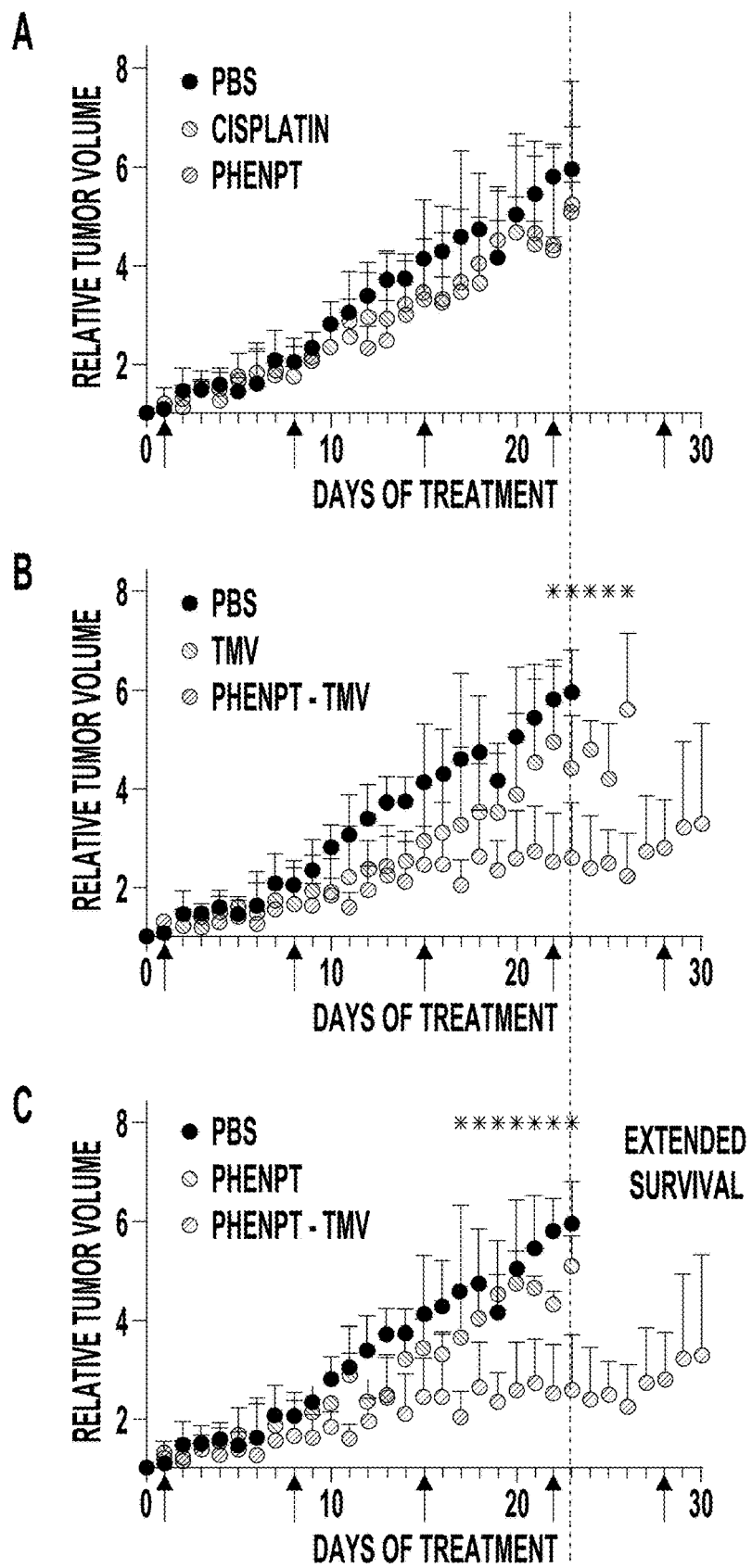
FIGS. 7A-C show treatment of MDA-MB-231 xenografts in an athymic mouse model. Treatment begun when tumors reached 250-300 mm$^3$; arrows indicate the treatment schedule; treatment was given by an intravenous bolus injection of 1.0 mg/kg of PhenPt-TMV, phenanthriplatin (PhenPt), cisplatin, TMV, or PBS; dosage was normalized to platinum content. Tumor volumes were monitored daily, and total volume was normalized to initial tumor size at time of treatment. Each treatment group consists of 5 animals (n=5); *indicates p<0.05.
Figure 8:
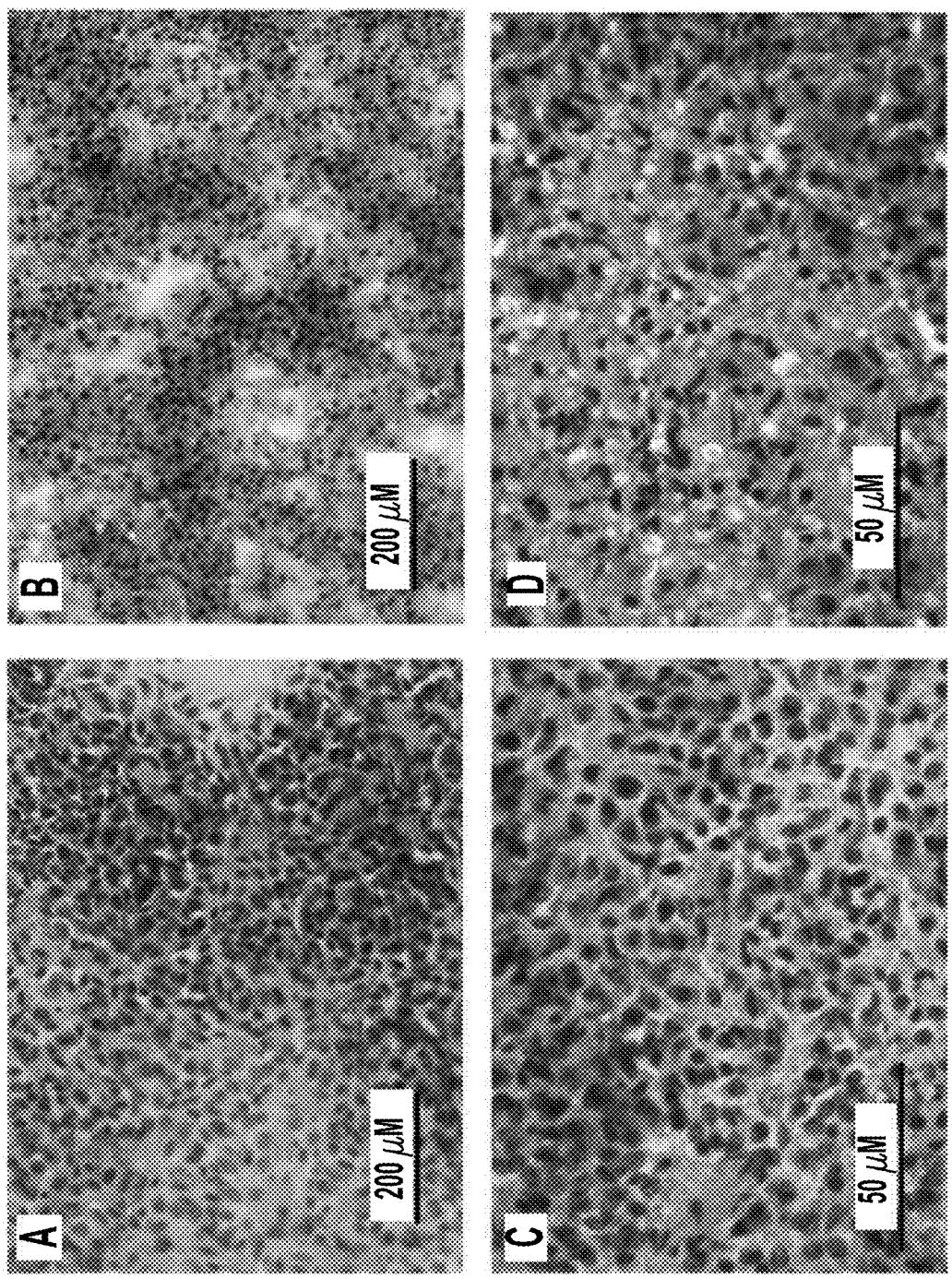
FIGS. 8A-D show histology of MDA-MB-231 tumor sections. H&E-stained tumor tissue sections from (FIGS. 8A and 8C) PBS treated and (FIGS. 8B and 8D) PhenPt-TMV treated animals. Tumors were collected and stained at the completion of the treatment.

The in vivo properties of PhenPt-TMV were assessed using a mouse model of triple negative breast cancer, MDA-MB-231 xenografts induced in NCR nu/nu mice. Weekly intravenous bolus injections using a dose of 1.0 mg/kg phenanthriplatin commenced when tumors reached a volume of 250-300 mm$^3$. Groups were treated with PhenPt-TMV, TMV, phenanthriplatin, or cisplatin (dosage was normalized to total platinum content), and a control group received PBS. PhenPt-TMV was freshly prepared, and the Pt content was confirmed by ICP-MS, prior to each injection. Disease burden, assessed by tumor volume, was monitored for 30 days (FIGS. 7A-C). Side effects were evaluated daily by examining the physical condition, body weight, and behavior of the animals.

The tumor treatment study showed that PhenPt-TMV outperformed free phenanthriplatin as well as the drug cisplatin, which were ineffective at a 1 mg/kg dose. Also, TMV treatment showed no statistically significant difference compared to PBS-treated control groups. Tumor growth rates of PhenPt-TMV-treated animals were significantly slower compared to treatment with free phenanthriplatin or TMV, indicating successful targeting and efficacy. PhenPt-TMV treated tumors were 4× smaller compared to tumors in the control groups. Free phenanthriplatin and TMV treatment had no effect (FIGS. 7A and 7C), and significant tumor burden, defined by volumes exceeding 10% of the animal's body weight, required termination of the experiment before completion of the study. Efficacy was also confirmed by histology. The intra-tumoral effects of PhenPt-TMV were evaluated using histology and hematoxylin and eosin (H&E) staining following completion of the study (FIGS. 8A-D). In addition to a reduction in overall tumor volume, tumors treated with PhenPt-TMV showed a reduced cellularity and apparent nuclear condensation, supporting intratumoral apoptosis caused by the action of phenanthriplatin within the tumor.

Cisplatin was less effective in the in vitro cell culture and in vivo assays performed here. In contrast, phenanthriplatin is highly effective in cell culture (FIGS. 5A-E), but lacks in vivo efficacy, highlighting the great value in the present viral delivery system. The TMV-based carrier appears to be a most promising candidate toward the goal of moving phenanthriplatin to the clinic.

Figure 9:
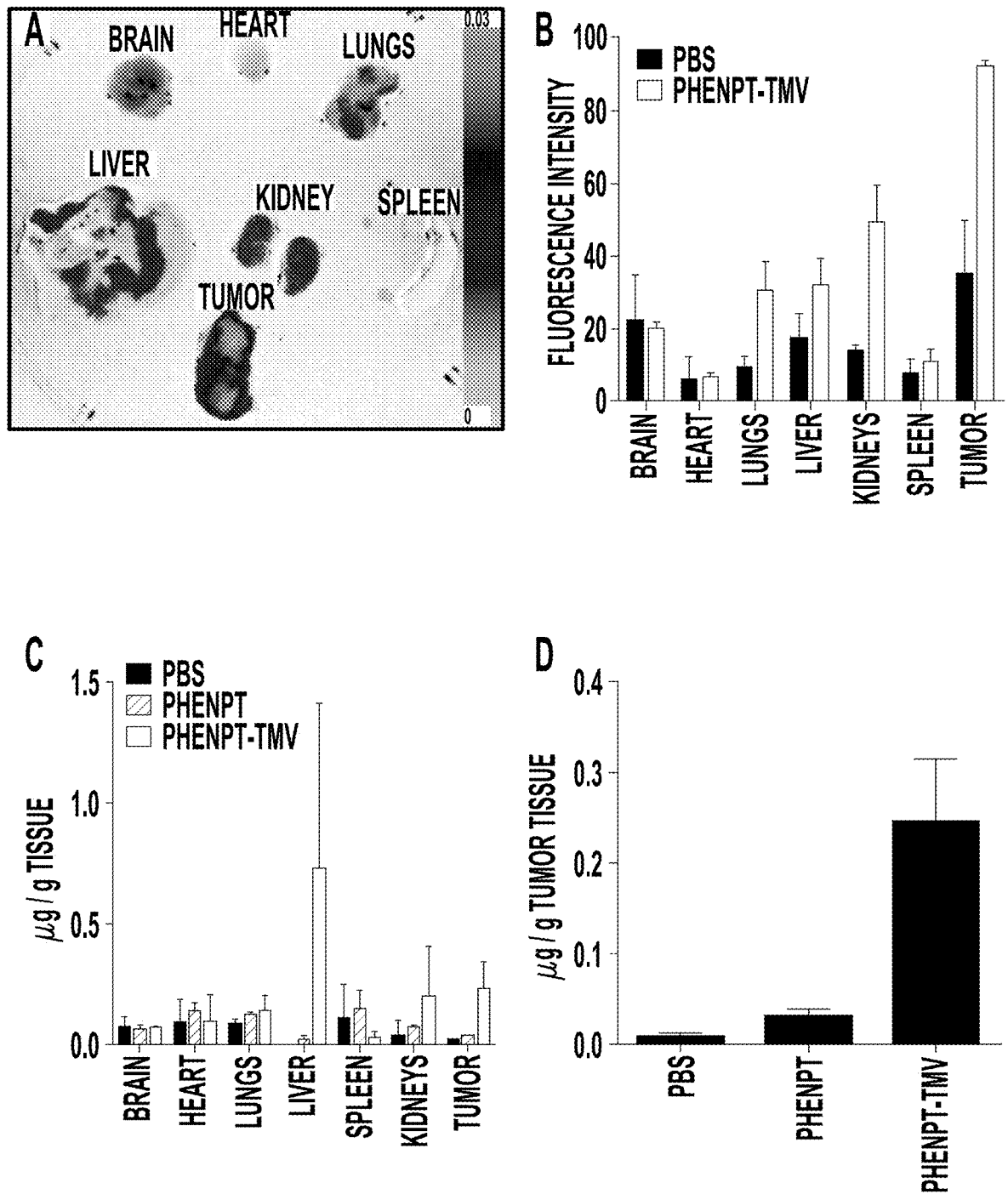
FIGS. 9A-D show biodistribution of PhenPt-TMV in MDA-MB-231 tumor bearing animals.

The biodistribution of PhenPt-TMV, including co-localization of phenanthriplatin and TMV, was evaluated 24 h post-administration using a combination of fluorescent imaging (Maestro Imager) and elemental analysis (Graphite Furnace Atomic Absorption Spectroscopy). To enable fluorescence imaging, TMV was labeled with sulfo-Cy5 dye at exterior tyrosine side chains as previously described, then loaded with phenanthriplatin. The phenanthriplatin loading efficiency was unaffected by exterior modification by the fluorophore, further supporting interior loading of this drug candidate. Imaging and region of interest (ROI) analysis indicated that PhenPt-TMV indeed targeted the tumor tissue (FIGS. 9A-B). This result can be explained by passive homing based on the enhanced permeability and retention (EPR) effect. The neovasculature required by rapidly growing tumors is more permeable than that of surrounding healthy tissue, leading to preferential accumulation of nanoparticles in tumor tissue. High-AR materials, such as TMV, exhibit increased tumor homing properties based on increased margination and tissue penetration properties.

Maestro imaging indicated that PhenPt-TMV also reaches nontarget organs. This biodistribution is expected from our earlier studies; proteinaceous nanoparticles are cleared through a combination of renal filtration and sequestration in organs of the mononuclear phagocyte system, the liver and spleen.

Platinum elemental analysis (FIGS. 9C-D) also confirmed successful delivery to the tumor tissue as well as clearance through the liver and kidneys. Over the course of the study, mice treated with PhenPt-TMV did not show any weight loss (FIG. 10A) or behavioral changes, indicating that the formulation is well tolerated with no apparent toxicity.

Figure 10:
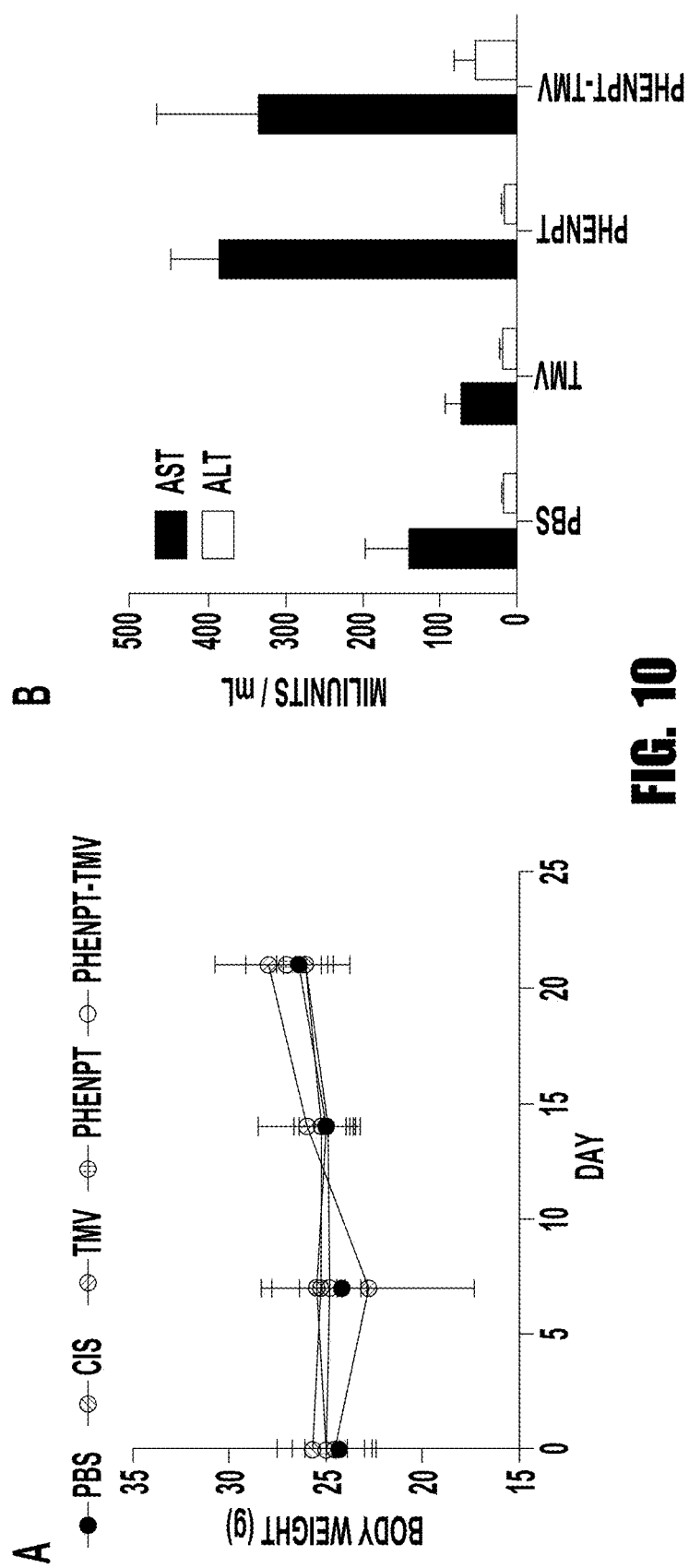
FIGS. 10A-C show toxicity of PhenPt-TMV in treated animals.
Figure 10C:
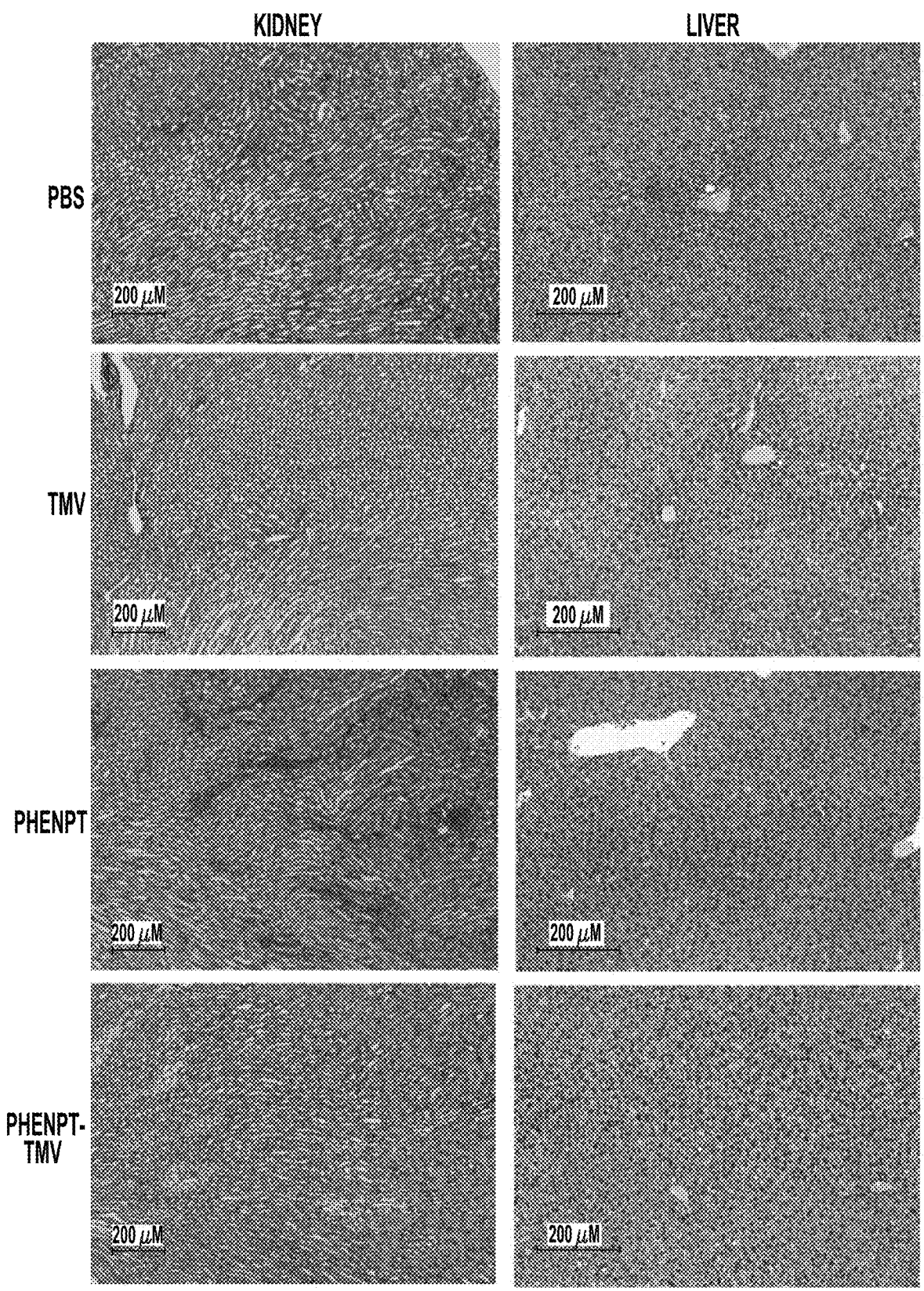
Figure 11:
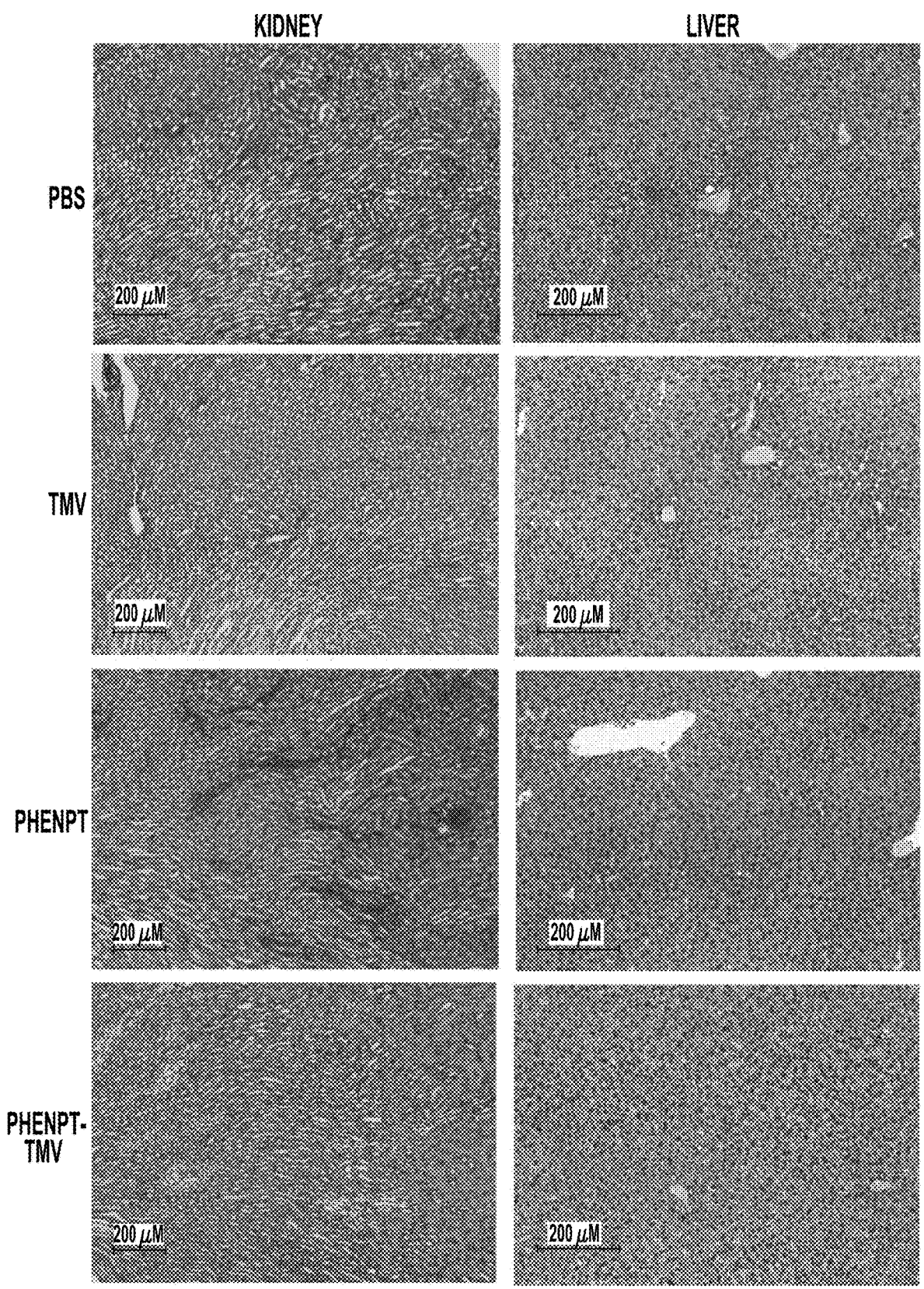

Overall, the biodistribution data support the efficacy study; the TMV delivery system targets the potent material to tumor tissue, enabling treatment. Systemic administration of phenanthriplatin is ineffective. The potential toxicology of PhenPt-TMV treatment compared to control groups was assessed by body weight monitoring, liver enzyme testing, and histology of liver and kidneys (FIGS. 10A-C). Balb/c mice were treated via intravenous injection with PBS, TMV, phenanthriplatin, or PhenPt-TMV at the same dosing schedule used for the efficacy studies (1.0 mg/kg phenanthriplatin or PhenPt-TMV, normalized for platinum content and TMV). Blood was collected by retro-orbital bleeds, 24 h following injection, and aspartate aminotransferase (AST) and alanine aminotransferase (ALT) levels were assessed (FIG. 10B). No significant changes in the levels of either enzyme were observed in the TMV group, however, both free PhenPt and PhenPt-TMV groups showed a significant increase in AST when compared to PBS. An increase in ALT level was observed for the PhenPt-TMV group; however, values recorded were within the normal range for this mouse breed (Charles River). Although ALT is a specific liver viability indicator, AST is less specific to liver. No significant changes in ALT levels were observed, consistent with histology indicating no apparent toxicity (FIGS. 10B-C). The increased AST levels may point to adverse effects induced in other organs, such as the kidneys. Indeed, histology staining indicated necrosis of epithelia on the proximal tubules as well as narrowing of the lumen (FIG. 10C), observed for phenanthriplatin and PhenPt-TMV treated groups. The data therefore indicate potential kidney damage, a common side effect for platinum-based chemotherapeutics, typically managed in human patients by hydration, sometimes accompanied by a diuretic. The lack of weight loss or changes in activity level of the treated animals suggests that adverse effects may be manageable throughout the course of treatment. Nephrotoxicity may also be reduced through coating of TMV with polyethylene glycol, a polymer that decreases clearance of viral nanoparticles through the kidney.

Another important future direction is the consideration of the potential immunotoxicity. Here we observed a slight delay in tumor growth in the TMV-treated group (FIG. 6B), which may be the result of innate immune cells activation. Future studies will utilize non-immune compromised mouse models to investigate the possibility of immuno-chemo combination therapies delivered through plant virus-based delivery.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, the inventors are not bound by theories described herein. The invention is not limited to the exact details shown and described, for variations obvious to one skilled in the art will be included within the invention defined by the claims.

What is claimed is:

1. An anticancer virus particle, comprising a tobacco mosaic virus particle and a cationic platinum-based anticancer agent and any carrier for the agent are non-covalently encapsulated within an interior channel of the tobacco mosaic virus particle.

2. The anticancer virus particle of claim 1, wherein the exterior surface of the tobacco mosaic virus particle has been PEGylated.

3. The anticancer virus particle of claim 1, wherein the cationic platinum-based anticancer agent is selected from the group consisting of satraplatin and picoplatin.

4. The anticancer virus particle of claim 1, wherein a targeting ligand is attached to the exterior of the tabacco mosaic virus particle.

5. A method of treating cancer in a subject identified as having cancer by administering to the subject a therapeutically effective amount of an anticancer virus particle, comprising a tobacco mosaic virus particle and a cationic platinum-based anticancer agent and any carrier for the agent are non-covalently encapsulated within an interior channel of the tobacco mosaic virus particle.

6. The method of claim 5, wherein the cancer is ovarian cancer, colon cancer, brain cancer, or breast cancer.

7. The method of claim 5, wherein the anticancer virus particle is administered together with a pharmaceutically acceptable carrier.

8. The method of claim 5, wherein the exterior surface of the tobacco mosaic virus particle has been PEGylated.

9. The method of claim 5, wherein the cationic platinum-based anticancer agent is selected from the group consisting of satraplation and picoplatin.

10. The method of claim 5, wherein a targeting ligand is attached to the exterior of the tobacco mosaic virus particle.

11. The anticancer virus particle of claim 3, wherein the cationic platinum-based anticancer agent is in aquated form.

12. The method of claim 9, wherein the cationic platinum-based anticancer is in aquated form.

* * * * *